US008697635B2

(12) United States Patent
Kim et al.

(10) Patent No.: US 8,697,635 B2
(45) Date of Patent: Apr. 15, 2014

(54) PHARMACEUTICAL PREPARATION TO BE ADMINISTERED INTO RESPIRATORY ORGANS FOR TREATING OR PREVENTING INFLAMMATORY RESPIRATORY DISEASES, AND METHOD FOR TREATING OR PREVENTING SUCH DISEASES

(75) Inventors: Yoon Keun Kim, Pohang-si (KR); Yong Song Gho, Pohang-si (KR); You Me Tae, Incheon (KR); Yoe Sik Bae, Busan (KR); Sung Ho Ryu, Pohang-si (KR)

(73) Assignee: Postech Academy-Industry Foundation, Pohang-Si, Gyeongsangbuk-Do (KR)

( * ) Notice: Subject to any disclaimer, the term of this patent is extended or adjusted under 35 U.S.C. 154(b) by 196 days.

(21) Appl. No.: 13/320,737

(22) PCT Filed: May 12, 2010

(86) PCT No.: PCT/KR2010/003015
§ 371 (c)(1),
(2), (4) Date: Nov. 15, 2011

(87) PCT Pub. No.: WO2010/131909
PCT Pub. Date: Nov. 18, 2010

(65) Prior Publication Data
US 2012/0060834 A1 Mar. 15, 2012

(30) Foreign Application Priority Data
May 15, 2009 (KR) .................. 10-2009-0042353

(51) Int. Cl.
*A61K 38/08* (2006.01)
(52) U.S. Cl.
USPC .......................... 514/2.3; 514/21.8
(58) Field of Classification Search
None
See application file for complete search history.

(56) References Cited

U.S. PATENT DOCUMENTS

| 8,479,728 | B2 * | 7/2013 | Longest et al. ........... 128/203.16 |
| 2003/0055001 | A1 * | 3/2003 | Bae et al. ................. 514/17 |
| 2003/0224987 | A1 | 12/2003 | Ryu et al. |
| 2004/0261140 | A1 | 12/2004 | Benson |
| 2006/0076010 | A1 * | 4/2006 | King ....................... 128/200.23 |
| 2007/0219139 | A1 * | 9/2007 | Sung-Ho et al. ............. 514/17 |
| 2007/0298116 | A1 * | 12/2007 | Bechtold-Peters et al. ... 424/499 |
| 2008/0202513 | A1 * | 8/2008 | Birchall et al. ........... 128/203.15 |
| 2008/0274978 | A1 | 11/2008 | Suh et al. |
| 2010/0249018 | A1 | 9/2010 | Bae et al. |
| 2012/0028941 | A1 * | 2/2012 | Cooper et al. ............... 514/171 |

FOREIGN PATENT DOCUMENTS

| KR | 10-2004-0012929 A | 2/2004 |
| WO | 03064447 A2 | 8/2003 |
| WO | 2005/077412 A | 8/2005 |
| WO | 2005075505 A1 | 8/2005 |
| WO | 2007073127 A1 | 6/2007 |
| WO | WO 2007144198 A2 * | 12/2007 |
| WO | 2009057982 A1 | 5/2009 |
| WO | WO 2009057982 A1 * | 5/2009 |

OTHER PUBLICATIONS

Atzori, et al., "Absense of Proteinase-Activated Receptor-1 Signaling in Mice Confers Protection from fMLP-Induced Goblet Cell Metaplasia", American Journal of Respiratory Cell and Molecular Biology, vol. 41, 2009, pp. 680-687.
Bae, et al., "Differential Activation of Formyl Peptide Receptor Signaling by Peptide Ligands", Molecular Pharmacology, vo. 64, No. 4, 2003, pp. 841-847.
Kang, et al., "The Synthetic Peptide Trp-Lys-Tyr-Met-Val-D-Met Inhibits Human Monocyte-Derived Dendritic Cell Maturation via Formyl Peptide Receptor and Formyl Peptide Receptor-Like 2", The Journal of Immunology, 2005, 175, pp. 685-692.
Li, et al., "The synthetic peptide WKYMVm attenuates the function of the chemokine receptors CCR5 and CXCR4 through activation of formyl peptide receptor-like 1", Blood, May 15, 2001, vol. 97, No. 10, pp. 2941-2947.
Matheson, et al., "Cigarette Smoking Increases Neutrophil Formyl Methionyl Leucyl Phenylalanine Receptor Numbers", American College of Chest Physicians, 2003, pp. 1642-1647.
Rot, et al., "A series of six ligands for the human formyl peptide receptor: Tetrapeptides with high chemotactic potency and efficacy", Proc. Natl, Acad, Scie, USA 84: 7967-7971, 1987.
Showell, et al., "The Structure-Activity Relations of Synthetic Peptides as Chemotactic Factors and Inducers of Lysosomal Enzyme Secretion for Neutrophils", The Journal of Experimental Medicine, vol. 143: 1154-1169, 1976.
Le, et al., "Pleiotropic roles of formyl peptide receptors", Cytokine Groth Factor Reviews, 12, 2001, 91-105.
Bae, et al., "The Synthetic Chemoattractant peptide, Trp-Lys-Try-Met-Val-D-Met, enchances moncyte survival via PKC-dependent Akt activation", Journal of Leukocyte Biology, vol. 71 Feb. 2002, pp. 329-338.
Christophe, et al., "The Synthetic Peptide Trp-Lys-Tyr-Met-Val-Met-NH2 Specifically Activates Neutrophils through FPRL1/Lipoxin A4 Receptors and is an Agonist for the Orphan Monocyte-expressed Chemoattractant Receptor FPRL2", The Journal of Biological Chemistry, vol. 276, No. 24, Jun. 15, 2001, pp. 21585-21593.
He, et al., "The Synthetic Peptide Trp-Lys-Tyr-Met-Val-D-Met Is a Potent Chemotactic Agonist for Mouse Formyl Peptide Receptor", The Journal of Immunology 165 (8): 4598-4605 (2000).

(Continued)

*Primary Examiner* — Jeffrey E Russel
(74) *Attorney, Agent, or Firm* — Knobbe, Martens, Olson & Bear LLP

(57) ABSTRACT

The present application relates to a pharmaceutical preparation to be administered into respiratory organs for treating or preventing inflammatory respiratory diseases, comprising a peptide which acts on formyl peptide receptors (FPRs) or receptors analogous thereto, in an amount which is effective in suppressing respiratory inflammation. The present application also relates to a method for treating or preventing inflammatory respiratory diseases by using the preparation, and to a kit containing the preparation. As compared with systemic administration of the peptide by injection, direct administration of the peptide to respiratory organs remarkedly improves the effect in suppressing respiratory inflammation.

21 Claims, 7 Drawing Sheets

(56) References Cited

OTHER PUBLICATIONS

Seo JK, et al., "A Peptide with Unique Receptor Specficity", The Journal of Immunology 158 (4): 1895-1901 (1997).

Seo JK, et al., "Distribution of the Receptor for a Novel Peptide Stimulating Phosphoinositide Hydrolysis in Human Leukocytes", Clinical Biochemistry, vol. 31, No. 3, pp. 137-141 (1998).

H. Kim, et al., "Enhanced bactericidal function yb WKYMVm in patients with acute leukemia", Leukemia Research 32 (5): 717-725 (2008).

H. Kim, et al., "Granulocyte function is stimulated by a novel hexapeptide, WKYMvm, in chemotherapy-treated cancer paitents", Experimental Hematlogoy 34 (4): 407-413 (2006).

International Search Report issued on Jan. 20, 2011 for International Application No. PCT/KR2010/003015.

Bae, et al, "Identification of peptides that antagonize formyl peptide receptor-like 1-mediated signaling", The Journal of Immunology, 2004, vol. 173, pp. 607-614.

Supplementary European Search Report dated Jul. 2, 2013 of the corresponding European Patent Application No. 10775111.7.

* cited by examiner a b a b

SEQUENCE LISTING

```
<160> NUMBER OF SEQ ID NOS: 30

<210> SEQ ID NO 1
<211> LENGTH: 6
<212> TYPE: PRT
<213> ORGANISM: Artificial Sequence
<220> FEATURE:
<223> OTHER INFORMATION: C-terminal amidated W-peptide

<400> SEQUENCE: 1

His Phe Tyr Leu Pro Met
  1               5

<210> SEQ ID NO 2
<211> LENGTH: 6
<212> TYPE: PRT
<213> ORGANISM: Artificial Sequence
<220> FEATURE:
<223> OTHER INFORMATION: C-terminal amidated W-peptide

<400> SEQUENCE: 2

Met Phe Tyr Leu Pro Met
  1               5

<210> SEQ ID NO 3
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (6)
<223> OTHER INFORMATION: D-Met

<400> SEQUENCE: 3

His Phe Tyr Leu Pro Met
  1               5

<210> SEQ ID NO 4
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
```

```
<222> LOCATION: (6)
<223> OTHER INFORMATION: D-Met

<400> SEQUENCE: 4

Trp Lys Tyr Met Val Met
 1               5

<210> SEQ ID NO 5
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (6)
<223> OTHER INFORMATION: D-Met

<400> SEQUENCE: 5

Trp Lys Gly Met Val Met
 1               5

<210> SEQ ID NO 6
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (6)
<223> OTHER INFORMATION: D-Met

<400> SEQUENCE: 6

Trp Lys Tyr Met Gly Met
 1               5

<210> SEQ ID NO 7
<211> LENGTH: 6
<212> TYPE: PRT
<213> ORGANISM: Artificial Sequence
<220> FEATURE:
<223> OTHER INFORMATION: C-terminal amidated W-peptide

<400> SEQUENCE: 7

Trp Lys Tyr Met Val Gly
 1               5

<210> SEQ ID NO 8
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (6)
<223> OTHER INFORMATION: D-Met

<400> SEQUENCE: 8

Trp Arg Tyr Met Val Met
 1               5

<210> SEQ ID NO 9
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
```

```
<221> NAME/KEY: MOD_RES
<222> LOCATION: (6)
<223> OTHER INFORMATION: D-Met

<400> SEQUENCE: 9

Trp Glu Tyr Met Val Met
  1               5

<210> SEQ ID NO 10
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (6)
<223> OTHER INFORMATION: D-Met

<400> SEQUENCE: 10

Trp His Tyr Met Val Met
  1               5

<210> SEQ ID NO 11
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (6)
<223> OTHER INFORMATION: D-Met

<400> SEQUENCE: 11

Trp Asp Tyr Met Val Met
  1               5

<210> SEQ ID NO 12
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (6)
<223> OTHER INFORMATION: D-Met

<400> SEQUENCE: 12

Trp Lys His Met Val Met
  1               5

<210> SEQ ID NO 13
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (6)
<223> OTHER INFORMATION: D-Met

<400> SEQUENCE: 13

Trp Lys Glu Met Val Met
  1               5

<210> SEQ ID NO 14
<211> LENGTH: 6
```

```
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (6)
<223> OTHER INFORMATION: D-Met

<400> SEQUENCE: 14

Trp Lys Trp Met Val Met
 1               5

<210> SEQ ID NO 15
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (6)
<223> OTHER INFORMATION: D-Met

<400> SEQUENCE: 15

Trp Lys Arg Met Val Met
 1               5

<210> SEQ ID NO 16
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (6)
<223> OTHER INFORMATION: D-Met

<400> SEQUENCE: 16

Trp Lys Asp Met Val Met
 1               5

<210> SEQ ID NO 17
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (6)
<223> OTHER INFORMATION: D-Met

<400> SEQUENCE: 17

Trp Lys Phe Met Val Met
 1               5

<210> SEQ ID NO 18
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (6)
<223> OTHER INFORMATION: D-Met

<400> SEQUENCE: 18

Trp Lys Tyr Met Tyr Met
```

<210> SEQ ID NO 19
<211> LENGTH: 6
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: VARIANT
<222> LOCATION: (5)
<223> OTHER INFORMATION: Xaa is Phe or Trp
<220> FEATURE:
<221> NAME/KEY: MOD_RES
<222> LOCATION: (6)
<223> OTHER INFORMATION: D-Met

<400> SEQUENCE: 19

Trp Lys Tyr Met Xaa Met
 1               5

<210> SEQ ID NO 20
<211> LENGTH: 6
<212> TYPE: PRT
<213> ORGANISM: Artificial Sequence
<220> FEATURE:
<223> OTHER INFORMATION: C-terminal amidated W-peptide

<400> SEQUENCE: 20

Trp Lys Tyr Met Val Glu
 1               5

<210> SEQ ID NO 21
<211> LENGTH: 6
<212> TYPE: PRT
<213> ORGANISM: Artificial Sequence
<220> FEATURE:
<223> OTHER INFORMATION: C-terminal amidated W-peptide

<400> SEQUENCE: 21

Trp Lys Tyr Met Val Val
 1               5

<210> SEQ ID NO 22
<211> LENGTH: 6
<212> TYPE: PRT
<213> ORGANISM: Artificial Sequence
<220> FEATURE:
<223> OTHER INFORMATION: C-terminal amidated W-peptide

<400> SEQUENCE: 22

Trp Lys Tyr Met Val Arg
 1               5

<210> SEQ ID NO 23
<211> LENGTH: 6
<212> TYPE: PRT
<213> ORGANISM: Artificial Sequence
<220> FEATURE:
<223> OTHER INFORMATION: C-terminal amidated W-peptide

<400> SEQUENCE: 23

Trp Lys Tyr Met Val Trp
 1               5

<210> SEQ ID NO 24
<211> LENGTH: 5
<212> TYPE: PRT
<213> ORGANISM: Artificial Sequence

```
<220> FEATURE:
<223> OTHER INFORMATION: C-terminal amidated W-peptide

<400> SEQUENCE: 24

Trp Lys Tyr Met Val
  1               5

<210> SEQ ID NO 25
<211> LENGTH: 5
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (5)
<223> OTHER INFORMATION: D-Met

<400> SEQUENCE: 25

Lys Tyr Met Val Met
  1               5

<210> SEQ ID NO 26
<211> LENGTH: 4
<212> TYPE: PRT
<213> ORGANISM: Artificial Sequence
<220> FEATURE:
<223> OTHER INFORMATION: C-terminal amidated W-peptide

<400> SEQUENCE: 26

Lys Tyr Met Val
  1

<210> SEQ ID NO 27
<211> LENGTH: 4
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (4)
<223> OTHER INFORMATION: D-Met

<400> SEQUENCE: 27

Tyr Met Val Met
  1

<210> SEQ ID NO 28
<211> LENGTH: 3
<212> TYPE: PRT
<213> ORGANISM: Artificial Sequence
<220> FEATURE:
<223> OTHER INFORMATION: C-terminal amidated W-peptide
<220> FEATURE:
<221> NAME/KEY: MOD_RES
<222> LOCATION: (3)
<223> OTHER INFORMATION: D-Met

<400> SEQUENCE: 28

Met Val Met
  1

<210> SEQ ID NO 29
<211> LENGTH: 4
<212> TYPE: PRT
<213> ORGANISM: Artificial Sequence
<220> FEATURE:
<223> OTHER INFORMATION: N-terminal formylated tetrapeptide
```

-continued

```
<400> SEQUENCE: 29

Met Ile Phe Leu
 1

<210> SEQ ID NO 30
<211> LENGTH: 4
<212> TYPE: PRT
<213> ORGANISM: Artificial Sequence
<220> FEATURE:
<223> OTHER INFORMATION: N-terminal formylated tetrapeptide

<400> SEQUENCE: 30

Met Leu Phe Ile
 1
```

PHARMACEUTICAL PREPARATION TO BE ADMINISTERED INTO RESPIRATORY ORGANS FOR TREATING OR PREVENTING INFLAMMATORY RESPIRATORY DISEASES, AND METHOD FOR TREATING OR PREVENTING SUCH DISEASES

TECHNICAL FIELD

The present invention relates to a pharmaceutical preparation, administrable via a respiratory route, for the treatment or prevention of inflammatory respiratory diseases, comprising an active ingredient a peptide binding to FPR (formyl peptide receptor) or its analog receptor, a kit comprising the pharmaceutical preparation, and a method for treating or preventing inflammatory respiratory diseases, using the same.

BACKGROUND ART

Respiratory disease encompasses pathological conditions that affect the organs and tissues responsible for respiration, such as the bronchi, lungs and so on, typically with the accompaniment of inflammation. Representative inflammatory respiratory diseases are acute upper respiratory tract infection, mediated by Th1 or Th17 immune response, chronic obstructive pulmonary disease (COPD), chronic sinusitis, allergic rhinitis, chronic lower respiratory tract infection, chronic bronchitis, emphysema, pneumonia, bronchial asthma, sequelae of pulmonary tuberculosis, acute respiratory distress syndrome, cystic fibrosis, and pulmonary fibrosis.

Inflammatory respiratory diseases may be treated or prevented by suppressing respiratory inflammation. However, there has still been a need for drugs which have a therapeutic effect on inflammatory respiratory diseases that is satisfactory.

The body has evolved to develop defense mechanisms against bacterial infection by N-formylmethionyl peptides produced from bacteria as chemoattractants for macrophages, especially neutrophils and monocytes. Among N-formyl peptides, f-Met-Leu-Phe (FMLP) was identified to have the most potent ability to induce phagocytosis and lysosomal enzyme release [Showell et al., J, Exp. Med, 143:1154-1169, 1976]. Since then, synthetic tetrapeptides, particularly, f-Met-Ile-Phe-Leu (SEQ ID NO: 29) and f-Met-Leu-Phe-Ile (SEQ ID NO: 30) were also reported to induce neutrophil reactions [Rot et al., Proc. Natl, Acad, Scie, USA 84:7967-7971, 1987]. In the beginning, the functions of the peptides were attributed to 1) N-terminal formyl group, 2) the side chain of methionine, and 3) the side chains of leucine and phenylalanine.

N-formyl peptide receptor (FPR) possesses seven hydrophobic transmembrane domains that are linked to adjacent ones via hydrophilic sequences located either within the cell or in an extracellular space (Murphy, Annu. Rev. Immunol. 12: 593-633, 1994). The first and the third intracellular loop are relatively small, consisting of five and six amino acid residues, respectively. While the carboxyl terminus is exposed in the cell, the N-terminus is exposed in the extracellular space. In addition, the intracellular sequences comprise a G protein-coupling region (essential for the function of the receptor) and a potential phosphorylation region.

The six amino acid sequence Trp-Lys-Tyr-Met-Val-d-Met (WKYMVm; SEQ ID NO: 4) is known to bind to FPR (formyl peptide receptor) and its analogues FPRL1 (formyl peptide receptor-like 1). Such a short peptide sequence shows high affinity for a broad spectrum of receptors and can be effectively used to study FPR- or FPRL1-mediated signaling [International Patent Publication No. WO/2005/077412; Le, Y., Oppenheim, J. J., and Wang, J. M. (2001) Cytokine Growth Factor Rev. 12, 91-105); Bae Y S et al., Journal of Leukocyte Biology 71(2): 329-338 (2002); Christophe T et al., Journal of Biological Chemistry 276(24): 21585-21593 (2001); He R et al., Journal of Immunology 165(8): 4598-4605 (2000); Li B Q et al., Blood 97(10): 2941-2947 (2001); Seo J K et al., Journal of Immunology 158(4): 1895-1901 (1997); Seo J K et al., Clinical Biochemistry 31(3): 137-141 (1998)].

However, there are not many examples in which peptides binding to FPR or its analog receptor are used to treat diseases. WKYMVm (SEQ ID NO: 4) was reported to increase the protective system against bacteria in patients with leukemia or cancer who had received chemotherapy [H. Kim et al., Leukemia Research 32(5):717-725 (2008); H. Kim et al., Experimental Hematology 34(4):407-413 (2006)]. There is disclosed a method for modulating immune responses using WKYMVm and peptides with similar amino acid sequence [WO2005/077412]. However, nowhere has the application of WKYMVm or other peptides binding to FPR or its analog receptors to the suppression of respiratory inflammation been disclosed in previous documents. Particularly, the fact that the administration of such peptides via the respiratory tract rather than via other routes can significantly suppress respiratory inflammation has not yet been reported.

DISCLOSURE

Technical Problem

Leading up to the present invention, intensive and thorough research was made into the treatment of inflammatory respiratory diseases, conducted by the present inventors, which resulted in the finding that when administered via the respiratory tract, certain peptides binding to FPR or its analog receptors have a great therapeutic effect on respiratory inflammation and thus are highly effective at treating and preventing inflammatory respiratory diseases.

It is technical objects of the present invention to provide a pharmaceutical preparation, administrable via a respiratory route, for the treatment or prevention of inflammatory respiratory diseases, comprising a peptide binding to FPR or its analog receptor as an active ingredient, a kit comprising the pharmaceutical preparation, and a method for treating or preventing inflammatory respiratory diseases using the same.

However, the technical objects to be achieved by the present invention are not limited to those mentioned above and other objects may be clearly understood by those skilled in the art from the description given below.

Technical Solution

In accordance with an aspect thereof, the present invention provides a pharmaceutical composition, able to be administered via a respiratory route, for the treatment or prevention of inflammatory respiratory diseases, comprising a pharmaceutically effective amount of a peptide or pharmaceutical salt thereof, acting as a ligand to a formyl peptide receptor (FPR) or its analog receptor, and a pharmaceutically or veterinarily acceptable carrier which is administrable via a respiratory route.

In accordance with another aspect thereof, the present invention provides a kit comprising the pharmaceutical preparation and a delivery device.

In accordance with a further aspect thereof, the present invention provides a method for the treatment or prevention of an inflammatory respiratory disease, comprising administering the pharmaceutical preparation to a subject in need thereof via a respiratory route.

Advantageous Effects

A pharmaceutical preparation comprising a peptide, acting as a ligand to formyl peptide receptor (FPR) or an analogous receptor, significantly suppressed respiratory inflammation when administered via a respiratory route, but no suppressive effects when intraperitoneally injected. That is, the therapeutic effect of the peptide on respiratory inflammation can be significantly enhanced when it is administered via the respiratory tract rather than a systemic route. Accordingly, a pharmaceutical preparation comprising a certain peptide, acting as a ligand to FPR or its analogous receptor, can be administered via a respiratory route to treat or prevent inflammatory respiratory diseases, exhibiting a significant suppressive effect on respiratory inflammation.

DESCRIPTION OF DRAWINGS

FIG. 3A shows CD4+IFN-γ levels. FIG. 3B shows BAL IP-10 levels. FIG. 3C shows BAL IL-12p40 levels.

FIG. 4A shows CD4+IL-17 levels. FIG. 4B shows BAL IL-17 levels.

FIG. 5A shows BAL IL-6 levels. FIG. 5B shows BAL TNF-α levels.

FIG. 7A shows BAL IL-12p40 levels. FIG. 7B shows BAL TGF-β levels.

FIG. 9A shows LN IFN-γ levels. FIG. 9B shows CD3+CD4+IFN-γ levels. FIG. 9C shows BAL IFN-γ levels.

FIG. 10A shows LN IL-17 levels. FIG. 10B shows CD3+CD4+IL-17 levels. FIG. 10C shows BAL IL-17 levels.

FIG. 11A shows CD3+CD4+IL-4 levels. FIG. 11B shows CD3+CD4+IL-10 levels.

FIG. 12A shows BAL IP-10 levels. FIG. 12B shows BAL IL-12p40 levels. FIG. 12C shows BAL TNF-α levels. FIG. 12D shows BAL IL-1β levels. FIG. 12E shows BAL MCP-1 levels. FIG. 12F shows BAL MIP-1 levels.

FIG. 15A shows BAL IL-17 levels. FIG. 15B shows BAL TGF-β levels.

FIG. 16A shows BAL IL-12p40 levels. FIG. 16B shows BAL IP-10 levels.

BEST MODE

Figure 1:
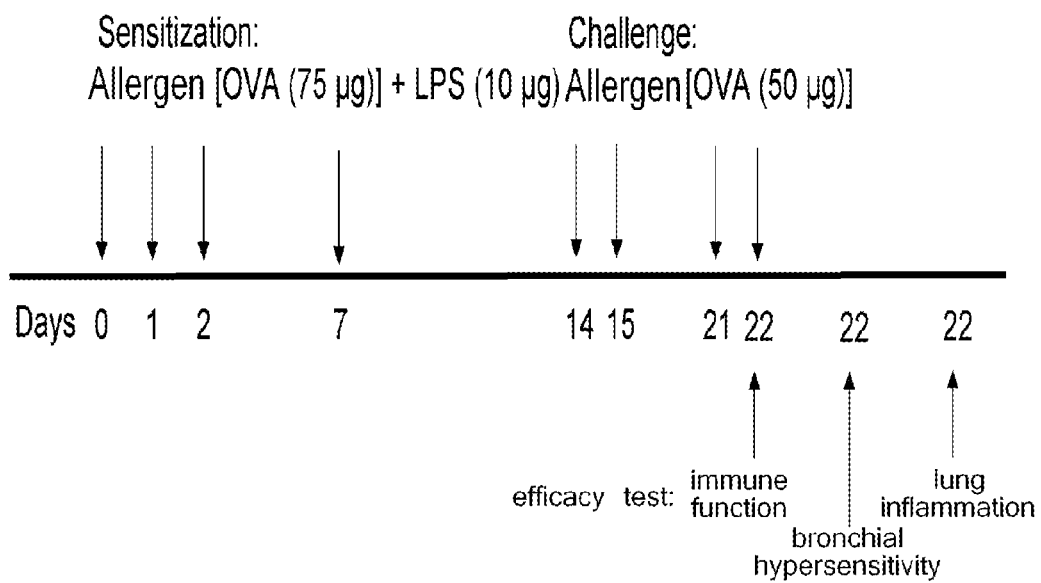
FIG. 1 is a schematic view showing the process of establishing an asthma animal model exhibiting Th1+Th17-mediated immune responses.

As used herein, the term "about" or "substantially" is intended to provide an allowance to accurate numerical restrictions. For example, the term "about" or "substantially" used in conjunction with the length of a peptide sequence means that amino acid sequences departing from the number of amino acids may be allowed. That is, so long as the amino acid sequences retain their functional activity, the number of amino acid residues may be altered by adding amino acid residues to the N- or C-terminus or deleting amino acid residues from the N- or C-terminus.

As used herein, the term "carrier" refers to a pharmaceutical vehicle, diluting agent or stabilizer which is nontoxic to cells or mammals exposed thereto in the dosages and concentrations employed. Pharmaceutically acceptable carriers may be aqueous pH buffer. Examples of the pharmaceutically acceptable carriers include buffers such as phosphate, citrate, and other organic acids; antioxidants such as ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates such as glucose, mannose, or dextrins; chelating agents such as EDTA; sugar alcohols such as mannitol, or sorbitol; salt-forming counter-ions such as sodium; and/or non-ionic surfactants such as TWEEN, polyethylene glycol (PEG) and PLURONICS, but are not limited thereto.

As used herein, the term "effective amount" or "effective dose" refers to an amount sufficient to provide a beneficial or desired clinical or biochemical result. An effective amount may be administered once or in more frequencies. For purposes of this invention, an effective amount of the active ingredient is an amount sufficient to alleviate, ameliorate, stabilize, reverse, reduce or delay the progress of a disease condition. In a preferred embodiment of the present invention, an "effective dose" is defined as the amount of a compound which can inhibit the binding of FPR family receptors and its agonist.

The term "FPR analogue," as used herein, may encompass, for example, FPRL1 (formyl peptide receptor-like 1), and FPRL2, but are not limited thereto.

The term "W-peptide," as used herein, refers to a ligand which has high affinity for FPR and its analogues, and may encompass peptides, polypeptides, and/or proteins, which contain the amino acid sequence of W-peptide, and may also encompass all possible mutants or fragments of the polypeptides containing the amino acid sequence of W-peptide.

With reference to the drawings, a detailed description will be given of the embodiment and examples of the present invention so that the artisan of ordinary skill in the art can easily implement the present invention. However, the present invention may be embodied in various different patterns and is not limited to the embodiments and examples explained herein. In the drawings, portions unrelated with the description are omitted for clarity and the same reference numerals are used throughout the different drawings to designate the same or similar components.

In accordance with an aspect thereof, the present invention provides a pharmaceutical preparation, able to be administered via a respiratory route, for the treatment or prevention of an inflammatory respiratory disease, comprising a peptide or a pharmaceutically acceptable salt thereof, acting as a ligand to formyl peptide receptor (FPR) or an FPR analogue, and a pharmaceutically or veterinarily acceptable carrier.

In one embodiment, the peptide is a W-peptide, for example, a hexapeptide. However, the present invention is not limited to hexapeptides. The peptide may be longer or shorter than hexapeptides. So long as the peptide functions to antagonize the signal pathway mediated by the formyl peptide receptor or its analog receptors, it may consist of 4 to 15 amino acids, preferably 4 to 10 amino acids, more preferably 4 to 7 amino acids, and even more preferably 6 amino acids. In a preferred embodiment, the peptide may have an amino acid sequence selected from the group consisting of amino acids sequences of SEQ ID NOS: 1 to 28 given in Table 1, below, but is not limited thereto. With regard to the peptides listed in Table 1, reference may be made to International Patent Publication No. WO/2005/077412. The peptide sequences are also expressed with standard abbreviations for amino acids in Table 1 wherein small letters represent D-residues. Functional derivatives, precursors, or pharmaceutically acceptable salts of the peptides fall within the scope of the present invention.

TABLE 1

| SEQ ID NO | Amino acid Sequence |
|---|---|
| 1 | His-Phe-Tyr-Leu-Pro-Met-CONH2; HFYLPM |
| 2 | Met-Phe-Tyr-Leu-Pro-Met-CONH2; MFYLPM |
| 3 | His-Phe-Tyr-Leu-Pro-D-Met-CONH2; HFYLPm |
| 4 | Trp-Lys-Tyr-Met-Val-D-Met-CONH2; WKYMVm |
| 5 | Trp-Lys-Gly-Met-Val-D-Met-NH2; WKGMVm |
| 6 | Trp-Lys-Tyr-Met-Gly-D-Met-NH2; WKYMGm |
| 7 | Trp-Lys-Tyr-Met-Val-Gly-NH2; WKYMVG |
| 8 | Trp-Arg-Tyr-Met-Val-D-Met-NH2; WRYMVm |
| 9 | Trp-Glu-Tyr-Met-Val-D-Met-NH2; WEYMVm |
| 10 | Trp-His-Tyr-Met-Val-D-Met-NH2; WHYMVm |
| 11 | Trp-Asp-Tyr-Met-Val-D-Met-NH2; WDYMVm |
| 12 | Trp-Lys-His-Met-Val-D-Met-NH2; WKHMVm |
| 13 | Trp-Lys-Glu-Met-Val-D-Met-NH2; WKEMVm |
| 14 | Trp-Lys-Trp-Met-Val-D-Met-NH2; WKWMVm |
| 15 | Trp-Lys-Arg-Met-Val-D-Met-NH2; WKRMVm |
| 16 | Trp-Lys-Asp-Met-Val-D-Met-NH2; WKDMVm |
| 17 | Trp-Lys-Phe-Met-Val-D-Met-NH2; WKFMVm |
| 18 | Trp-Lys-Tyr-Met-Tyr-D-Met-NH2; WKYMYm |
| 19 | Trp-Lys-Tyr-Met-(Phe/Trp)-D-Met-NH2; WKYM(F/W)m |
| 20 | Trp-Lys-Tyr-Met-Val-Glu-NH2; WKYMVE |
| 21 | Trp-Lys-Tyr-Met-Val-Val-NH2; WKYMVV |
| 22 | Trp-Lys-Tyr-Met-Val-Arg-NH2; WKYMVR |
| 23 | Trp-Lys-Tyr-Met-Val-Trp-NH2; WKYMVW |
| 24 | Trp-Lys-Tyr-Met-Val-NH2; WKYMV |
| 25 | Lys-Tyr-Met-Val-D-Met-NH2; KYMVm |
| 26 | Lys-Tyr-Met-Val-NH2; KYMV |
| 27 | Tyr-Met-Val-D-Met-NH2; YMVm |
| 28 | Met-Val-D-Met-NH2; MVm |

In another embodiment of the present invention, the peptide may have the amino acid sequence of SEQ ID NO: 4, but is not limited thereto.

In another embodiment of the present invention, the carrier is in a gas, liquid or solid phase.

In another embodiment of the present invention, the pharmaceutical preparation may be administered intranasally, intrapulmonarily, intrabronchially, by inhalation or by respiration.

In another embodiment of the present invention, the pharmaceutical preparation may be in the form of an aerosol or spray comprising liquid or solid particles in which the carrier is impregnated with the peptide.

In another embodiment of the present invention, the pharmaceutical preparation may be in the form of inhalable or respirable particles with a diameter of about 10 μm or smaller in which the carrier is impregnated with the peptide.

In another embodiment of the present invention, the pharmaceutical preparation may be in the form of intranasally, intrapulmonarily or intrabronchially administrable particles with a diameter of about 100 μm or smaller in which the carrier is impregnated with the peptide.

In accordance with another aspect thereof, the present invention provides a kit comprising the pharmaceutical preparation, administrable via a respiratory route, of the present invention and a delivery device for pulmonary delivery of the pharmaceutical preparation.

In one embodiment of the present invention, the delivery device may include an aerosol or spray generator, but is not limited thereto.

In another embodiment of the present invention, the aerosol generator may include an inhaler, but is not limited thereto.

In another embodiment of the present invention, the inhaler may be a metered dose inhaler, but is not limited thereto.

In another embodiment of the present invention, the inhaler may include a nebulizer or an insufflator, but is not limited thereto.

In the kit according to another embodiment of the present invention, the delivery kit may be a compressed gas inhaler and the preparation may be in the form of an aqueous or non-aqueous suspension or a solution or water-in-oil or oil-in-water emulsion.

In another embodiment of the present invention, the kit is provided in a capsule, cartridge or blister, which may be a pierceable or openable capsule, cartridge or blister.

In another embodiment of the present invention, the delivery device may be pressurized and may operate with the aid of a propellant.

In the present invention, a peptide, all acting as a ligand to FPR or its analogous receptor, a functional derivative, precursor or pharmaceutically acceptable salt thereof, can be delivered into the respiratory system of a subject by inhalation, by respiration or by intranasal administration or into the lung by intrapulmonary instillation using a suitable means. Preferably, the active ingredient may be administered in the form of a powder or liquid aerosol or spray which can be inhaled intranasally or by pulmonary respiration or aspiration. Respirable or inhalable particles comprising the peptide, acting as a ligand to FPR or its analogous receptor, are delivered into the respiratory tract or the lung by the subject, that is, by inhalation or by intranasal administration or instillation. For example, the pharmaceutical preparation, administrable via a respiratory route, may comprise respirable or inhalable liquid or solid particles of the peptide which are sufficiently small that they can be inhaled through the oral cavity and the larynx and maintained within the bronchus and pulmonary alveoli. Typically, the particles used in the pharmaceutical preparation to be administered via a respiratory route in accordance with the present invention have a diameter of about 10 μm or less, for example, about 0.05, about 0.1, about 0.5, about 1, about 2 to about 4, about 6, about 8, about 10 μm.

In greater detail, particles ranging in size from about 0.5 to about 5 μm are respirable or inhalable. When sprayed or aerosolized in the mouth or nose, particles with irrespirable sizes tend to be deposited at the throat and swallowed. The content of irrespirable particles in the aerosol should be preferably minimized. For intranasal administration or pulmonary instillation, particles with a size of about 8, about 10, about 20, about 25 to about 35, about 50, about 100, about 150, about 250, and about 500 μm are advantageous because they are sure to stray in the nasal cavity or can be instilled and deposited into the lung. Particularly when applied to newborns or children, liquid preparations may flow out of the respiratory tract (nose) and the lung.

For example, when given as an aerosol, the pharmaceutical preparation for respiratory administration may be prepared by combining the peptide with a stable vehicle, e.g., water that is free of pyrogens. For pharmaceutical preparations containing respirable micro-sized, solid particles of the peptide may be prepared by pulverizing granules of the active compound with a mortar or a pestle, and passing the powder through a 400 mesh screen. When the pharmaceutical preparation is provided in an aerosol form, the solid micro-sized particles may be combined with a dispersant. Preferable is lactose. This preferable dispersant may be mixed at a weight ratio of 1:1 with the active compound, that is, the peptide. A liquid aerosol form of the peptide is suitable for use with a nebulizer [see, e.g., U.S. Pat. No. 4,501,729]. A nebulizer is a commercially available device used to administer medication in the form of a mist inhaled into the lungs, and uses oxygen, compressed air or ultrasonic power to break up medical solutions or suspensions into small aerosol droplets that can be directly inhaled from the venturi orifice of the device. A pharmaceutical preparation suitable for use with a nebulizer comprises the peptide in an amount of 40% w/w or less and preferably in an amount of 20% w/w or less. Typically, the preparation may comprise a carrier, typically water or a diluted alcohol solution which is preferably isotonic to the body fluid by containing sodium chloride. Optionally, the preparation may comprise an additive, such as a preservative, e.g., methyl hydroxybenzoate if the composition is not sterilized, an anti-oxidant, a fragrant, a volatile oil, a buffer, and a surfactant. The aerosol formulation containing solid particles of the peptide may be prepared using a solid micropaticle aerosol generator. Aerosol generators designed to administer solid microparticle drugs to a subject generate inhalable or respirable particles, as explained above, at a speed suitable to produce a volume containing a predetermined metered dose. Examples of the aerosol generators include metered dose inhalers and insufflators.

In accordance with another aspect thereof, the present invention provides a method for treating or preventing an inflammatory respiratory disease, comprising administering the pharmaceutical preparation, administrable via a respiratory route, to the respiratory tract of a mammal subject.

In one embodiment of the present invention, the method for treating or preventing an inflammatory respiratory disease comprises administering the pharmaceutical preparation intranasally, intrapulmonarily, by inhalation or by respiration.

In another embodiment of the present invention, the inflammatory respiratory disease may be selected from the group consisting of acute upper respiratory tract infection, a Th1/Th17-biased inflammatory respiratory disease, chronic obstructive pulmonary disease (COPD), chronic sinusitis, allergic rhinitis, chronic lower respiratory tract infection, emphysema, pneumonia, bronchial asthma, sequelae of pulmonary tuberculosis, acute respiratory distress syndrome, cystic fibrosis, pulmonary fibrosis and a combination thereof, but are not limited thereto.

In another embodiment of the present invention, the acute upper respiratory tract infection may be selected from the group consisting of a cold, acute pharyngitis, acute rhinitis, acute paranasal sinusitis, acute tonsillitis, acute laryngitis, acute epiglottitis, acute bronchitis and a combination thereof.

In another embodiment of the present invention, the chronic lower respiratory tract infection may be selected from the group consisting of chronic bronchitis, diffuse panbronchiolitis, bronchiectasis, and a combination thereof.

In another embodiment of the present invention, the inflammatory respiratory disease may be allergic rhinitis.

In another embodiment of the present invention, the inflammatory respiratory disease may be a Th1/Th17-based inflammatory respiratory disease.

In another embodiment of the present invention, the inflammatory respiratory disease may be chronic obstructive pulmonary disease (COPD).

According to the present invention, the pharmaceutical preparation, administrable via a respiratory route, comprising a peptide, acting as a ligand to FPR or its analogous receptor, as an active ingredient, is administered through the respiratory tract to suppress respiratory inflammation, exhibiting a therapeutic or prevention effect on inflammatory respiratory diseases.

The peptide acting as a ligand to FPR or its analogous receptor may be administered in a single dose or multiple discrete doses or in a continuous manner.

In the pharmaceutical preparation administrable via a respiratory route, the peptide acting as a ligand to FPR or its analogous receptor may be contained in a broad range of amounts. For example, the peptide may be used in an amount of about 0.001%, about 1%, about 2%, about 5%, about 10%, about 20%, about 40%, about 90%, about 98%, or about 99.999% based on the total amount of the pharmaceutical preparation. When additional drugs and additives are employed, the content of the peptide may be adjusted. The dose of the peptide may vary depending on the patient's age and weight and the type of diseases.

As an active gradient in the pharmaceutical preparation administrable via a respiratory route, the peptide acting as a ligand to FPR or its analogous receptors may be administered at a dose of from about 0.001 mg/kg/d to about 100 mg/kg/d in accordance with the present invention. In one embodiment, the dose of the peptide may range from about 0.1 mg/kg/d to about 100 mg/kg/d. In another embodiment, the dose ranges from about 1 mg/kg/d to about 10 mg/kg/d. A dose of the peptide for a specific patient may be determined depending on various factors including the activity and toxicity of the active ingredient employed; the patient's age, weight, general health, gender and diet; the time of administration; the rate of excretion; drug combinations; the severity of diseases; and the route of administration. Typically, in vitro dose-effect study results provide useful guidelines for administration doses. Also, studies in animal models are also useful. Factors taken into consideration to determine suitable doses are well known in the art and may be determined by the attending physician.

A better understanding of the present invention may be obtained through the following examples which are set forth to illustrate, but are not to be construed as limiting the present invention.

EXAMPLES

In the following Example and Comparative Example, the therapeutic effect of WKYMVm was evaluated in asthma animal models suffering from Th1- and Th17-mdiated immune response.

Comparative Example 1

Assay for Therapeutic Efficacy of WKYMVm (SEQ ID NO 4) upon Systemic Administration by Intraperitoneal Injection To establish an asthma animal model exhibiting TH1+TH17 immune responses, BALB/c mice (female, 6 weeks old), divided into groups (test group and positive control), each consisting of five, were sensitized and then intranasally administered with 75 µg of ovalbumin (OVA), as an allergen, and combination with 10 µg of LPS (lipopolysaccharide) as an adjuvant. This sensitization was performed on Day 0, 1, 2 and 7. When the allergen (OVA, 50 µg) was intranasally administered to the anesthetized mice on Days 14, 15, 21 and 22, WKYMVm was intraperitoneally injected at a dose of 4 mg/kg to the mice of the test group. Meanwhile, the mice of the positive control were intraperitoneally administered with the same dose of phosphate-buffered saline (PBS). For a negative control, the sensitization on Day 0, 1, 2 and 7 and the challenge on Day 14, 15, 21, and 22 were conducted in the same manner as in the positive control, except that PBS was used instead of the allergen. The establishment of the asthma mouse model is schematically shown in FIG. 1.

Twenty four hours after the final administration of the allergen (Day 23), the mice were examined for bronchial hypersensitivity to methacholine. In this context, the mice were placed in a chamber and allowed to inhale PBS for 3 min with the aid of a nebulizer, followed by measuring penh (enhanced pause) values for 3 min by means of non-invasive whole body plethysmography (Allmedicus, Korea). Likewise, the mice were allowed to inhale 6.25, 12.5, 25 and 50 mg/ml methacholine PBS sequentially, after which penh values for each concentration were measured. A mean of the penh values measured for 3 min was used as an index of airway obstruction.

Pulmonary inflammation was examined 6 hours (Day 22) and 48 hours (Day 24) after the final administration of the allergen. On Days 22 and 24, after mice were anesthetized by intraperitoneally injecting a mixture of ketamine and xylazine thereto, they were subjected to thoracotomy to expose the trachea into which a catheter was then inserted. After suturing the mice, 1 mL of germ-free PBS was infused twice to wash the airway to give bronchoalveolar lavage fluid (hereinafter referred to as "'BAL fluid"). For analyzing T-lymphocytes in lung tissues, the lung was excised and cells were extracted from local lymph nodes.

Following centrifugation of the BAL fluid at 3000 rpm and at 4° C. for 10 min, the cell pellet thus formed was suspended in PBS, and rolled on slide using a cytospin and stained with Diff Quick. More than 300 inflammatory cells were observed under an optical microscope with 10,000-fold magnification to determine cell counts by cell types, that is, macrophage, lymphocyte, neutrophil, and eosinophil. In the BAL fluid, the cytokines involved in Th1-mediated inflammation, such as gamma interferon, interferon-g-inducible protein 10 (IP-10), and IL-12, the cytokines involved in Th2-mediated inflammation, such as interleukin IL-4 and IL-13, the cytokines involved in Th17-mediated inflammation, such as IL-17, TNF-α and IL-6, and the cytokines involved in Th2- and Th17-mediated inflammation, such as TGF-β, were quantified using ELISA.

The excised pulmonary tissue was treated with collagenase type IV (Sigma) to separate cells therefrom. The cells were surface stained with anti-CD3, anti-CD4, and anti-CD8 antibodies (BD Pharmingen), all being conjugated with a fluorescent and the membrane was perforated with Triton, followed by intracellular cytokine staining with anti-IFN-γ, anti-IL-17, anti-IL-10 and anti-IL-4 antibodies. Types of the T lymphocytes introduced into the lung were analyzed using the fluorescence activated cell scanner FACSCalibur (Becton Dickinson).

After the cells extracted from the lymph nodes were incubated for 72 hours in PBS containing 100 μg/ml OVA, gamma interferon, IL-17 and IL-4, which are the cytokines involved in Th1-, Th17- and Th2-mediated inflammation, were quantified using ELISA.

Figure 2:
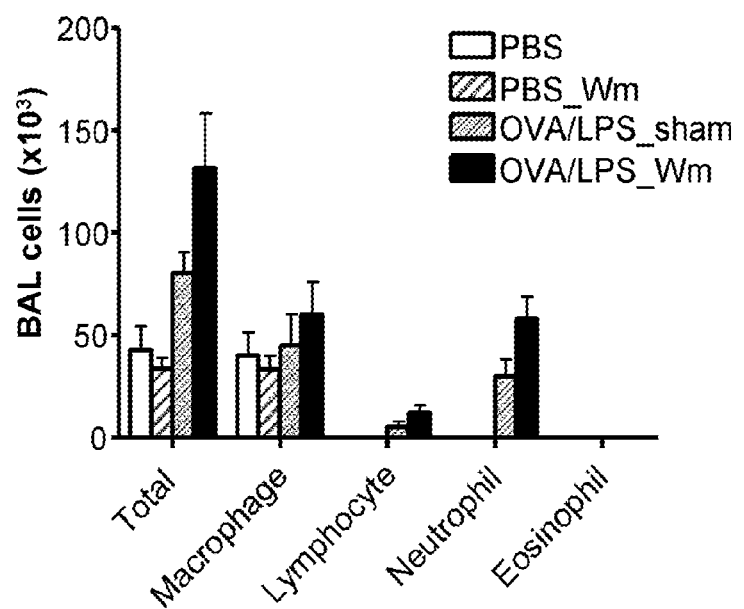
FIG. 2 is a graph of inflammatory cell counts in bronchoalveolar lavage fluid, showing inflammatory responses at 6 hours (Day 22) after the final administration of the allergen to the asthma mouse models intraperitoneally injected with the peptide acting as a ligand to FPR.
Figure 3:
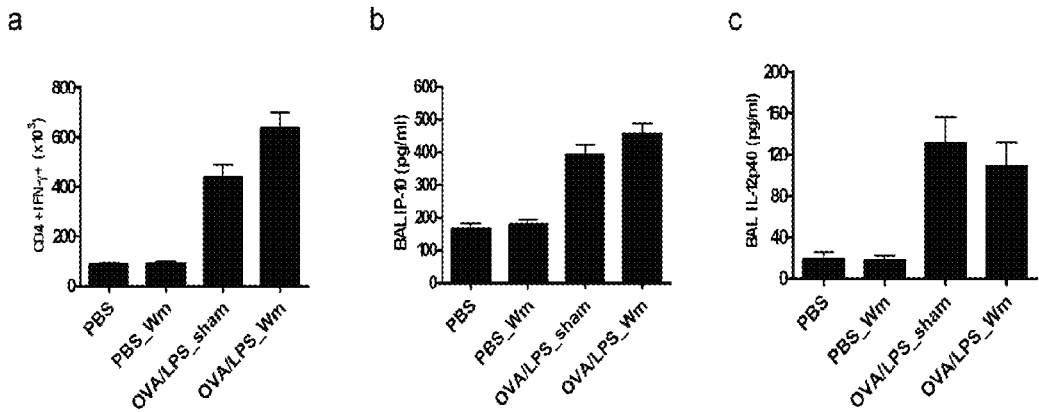
FIGS. 3A-3C are graphs of cytokine expression levels in bronchoalveolar lavage fluid, showing Th1-mediated inflammatory responses at 6 hours (Day 22) after the final administration of the allergen to the asthma mouse models intraperitoneally injected with the peptide acting as a ligand to FPR.
Figure 4:
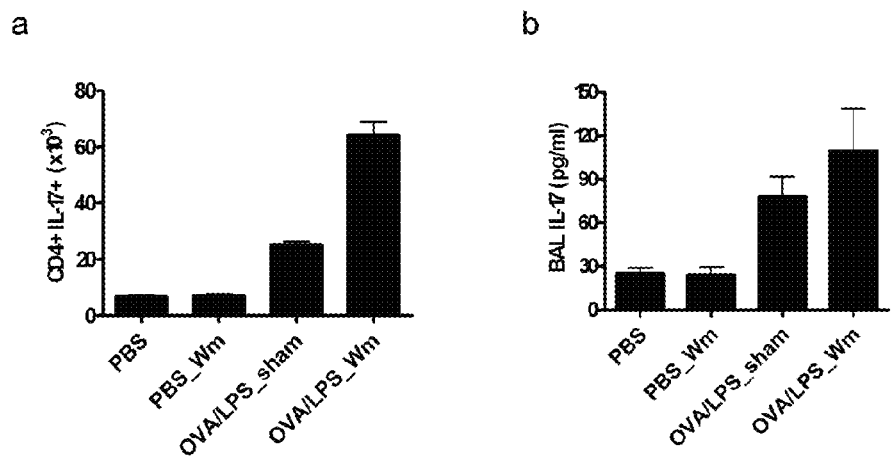
FIGS. 4A and 4B are graphs of cytokine expression levels in bronchoalveolar lavage fluid, showing Th17-mediated inflammatory responses at 6 hours (Day 22) after the final administration of the allergen to the asthma mouse models intraperitoneally injected with the peptide acting as a ligand to FPR.
Figure 5:
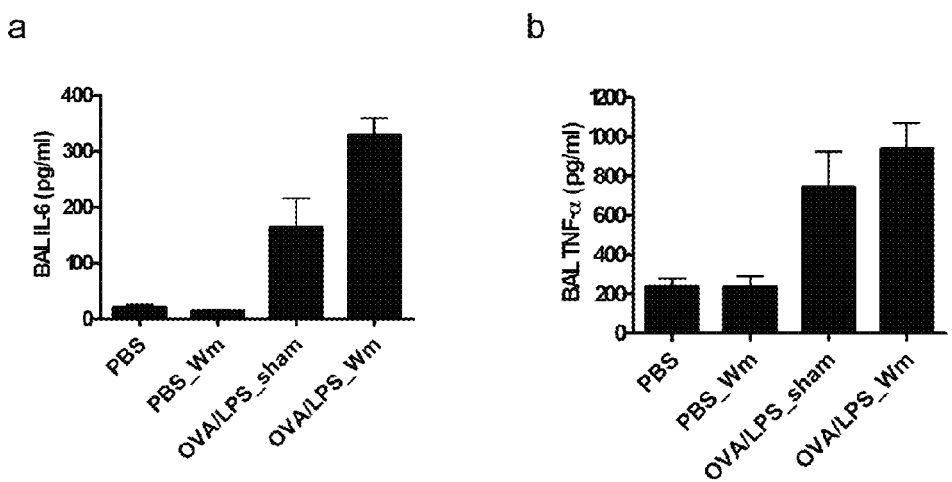
FIGS. 5A and 5B are graphs of cytokine levels in the bronchoalveolar lavage fluid released from inflammatory cells infiltrated by Th17- and IL-17-mediated inflammatory responses at 6 hours (Day 22) after the final administration of the allergen to the asthma mouse models intraperitoneally injected with the peptide acting as a ligand to FPR.

FIG. 2 shows cell counts obtained on Day 22, that is, 6 hours after the final administration of allergen. The BAL fluid from the asthma models sensitized with OVA and LPS was increased in inflammatory cell count, compared to that from the negative control sensitized with the allergen alone, irrespective of the intraperitoneal administration of the peptide (FIG. 2). The mice sensitized with the allergen and LPS were observed to increase in inflammatory cell count upon the systemic administration of W-peptide (test group), compared to sham administered (positive control). In addition, the inflammatory cells separated from the pulmonary tissue increased the release of gamma interferon (FIG. 3a), which was accompanied by increased levels of IP-10 (FIG. 3b) and IL-12p40 (FIG. 3c) in the BAL fluid. Further, among the inflammatory cells separated from the pulmonary tissues, CD4+ T cells in which IL-17 is expressed were found to increase in number (FIG. 4a), together with the level of IL-17 released to the BAL fluid (FIG. 4b). These changes were accompanied by increased levels of IL-6 (FIG. 5a) and TNF-α (FIG. 5b), both regarded as the downstream molecules of IL-17, in the BAL fluid.

Figure 6:
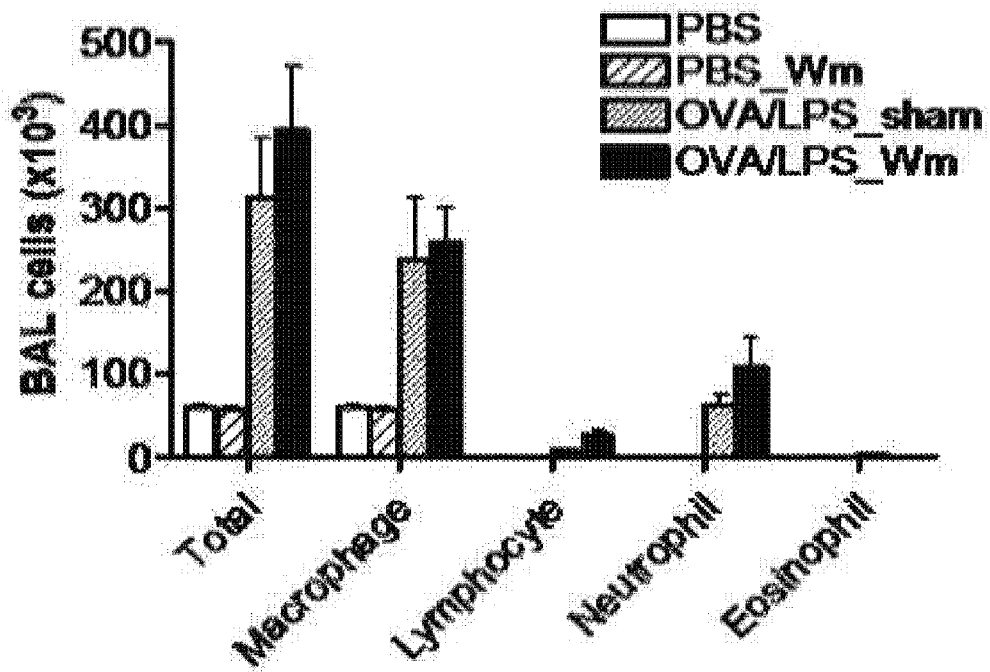
FIG. 6 is a graph of inflammatory cell counts in bronchoalveolar lavage fluid, showing inflammation at 48 hours (Day 24) after the final administration of the allergen to the asthma mouse models intraperitoneally injected with the peptide acting as a ligand to FPR.
Figure 7:
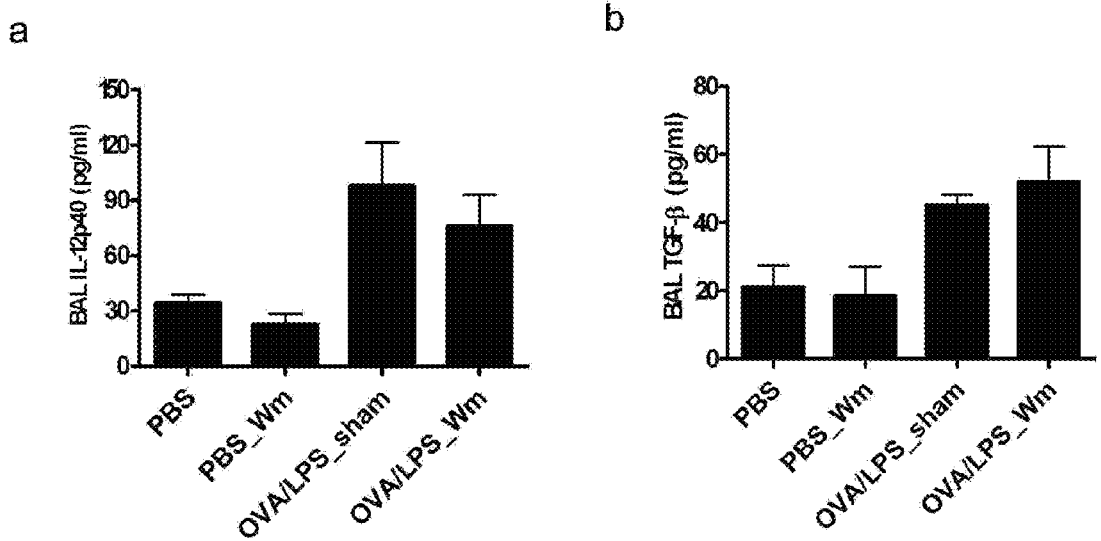
FIGS 7A and 7B show graphs of cytokine expression levels in bronchoalveolar lavage fluid from inflammatory cells infiltrated by Th1- and Th17-mediated inflammatory responses at 48 hours (Day 24) after the final administration of the allergen to the asthma mouse models intraperitoneally injected with the peptide acting as a ligand to FPR.

FIGS. 6 and 7 show results measured on Day 24, that is, 48 hours after the final administration of the allergen. As can be seen in FIG. 6, the inflammatory cell count in BAL, used as an index of pulmonary inflammation, was increased in the mice sensitized with the allergen and LPS, compared to the negative control administered with the allergen alone, but there was a difference between the allergen and LPS-sensitized mice systemically administered with W-peptide and a sham. Also, FIG. 7 indicates that no significant differences in the level of IL-12p40 (FIG. 7a) and TGF-β (FIG. 7b) were found between the allergen- and LPS-sensitized mice systemically administered with W-peptide (test group) and a shame (positive group), as measured by ELISA. Because the levels of IL-12p40 and TGF-β represent Th1- and Th17/Th2-mediated immune responses, respectively, the systemic administration did not ameliorate pulmonary inflammation.

Example 1

Assay for Therapeutic Efficacy of WKYMVm (SEQ ID NO 4) upon Intranasal Administration The assay was performed in the same manner as in the Comparative Example, except that WKYMVm was administered intranasally instead of intraperitoneally. On Days 14, 15, 21 and 22, the allergen [OVA 50 μg] was challenged, together with 200 μg/kg WKYMVm, into the nasal cavity. The other procedure was performed in the same manner as in the Comparative Example.

Figure 8:
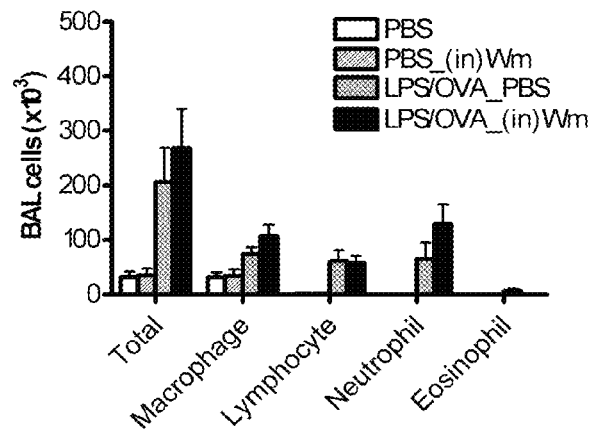
FIG. 8 is a graph showing the inflammatory response results assayed in the bronchoalveolar lavage fluid of the asthma mouse models intranasally administered with the peptide acting on FPR at 6 hours (Day 22) after the allergen was administered on Day 21.
Figure 9:
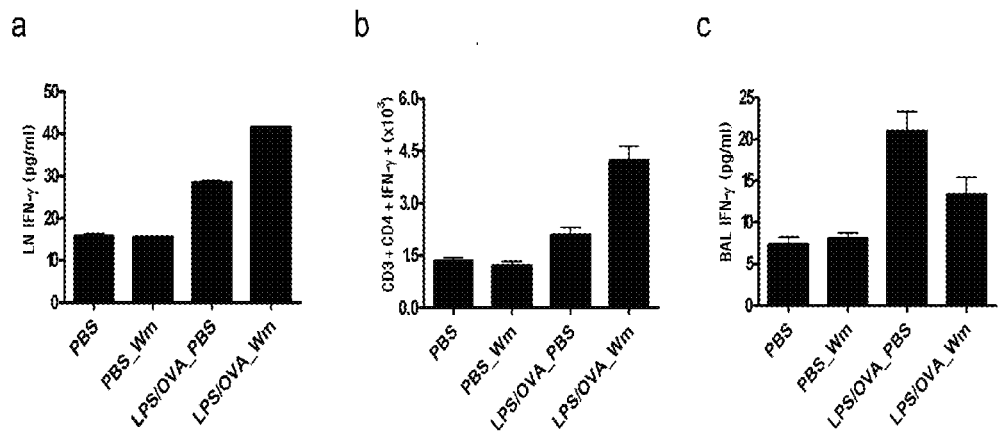
FIGS. 9A-9C are graphs showing the Th1-mediated immune response assayed in local lymph nodes, pulmonary tissues and bronchoalveolar lavage fluid of the asthma mouse models intranasally administered with the peptide acting on FPR at 6 hours (Day 22) after the allergen was administered on Day 21.
Figure 10:
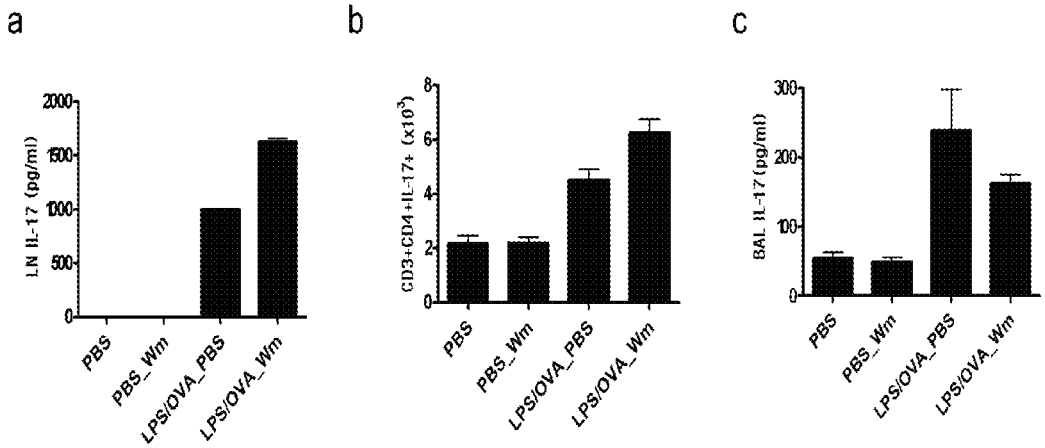
FIGS. 10A-10C are graphs showing the Th17-mediated immune response assayed in local lymph nodes, pulmonary tissues and bronchoalveolar lavage fluid of the asthma mouse models intranasally administered with the peptide acting on FPR at 6 hours (Day 22) after the allergen was administered on Day 21.
Figure 11:
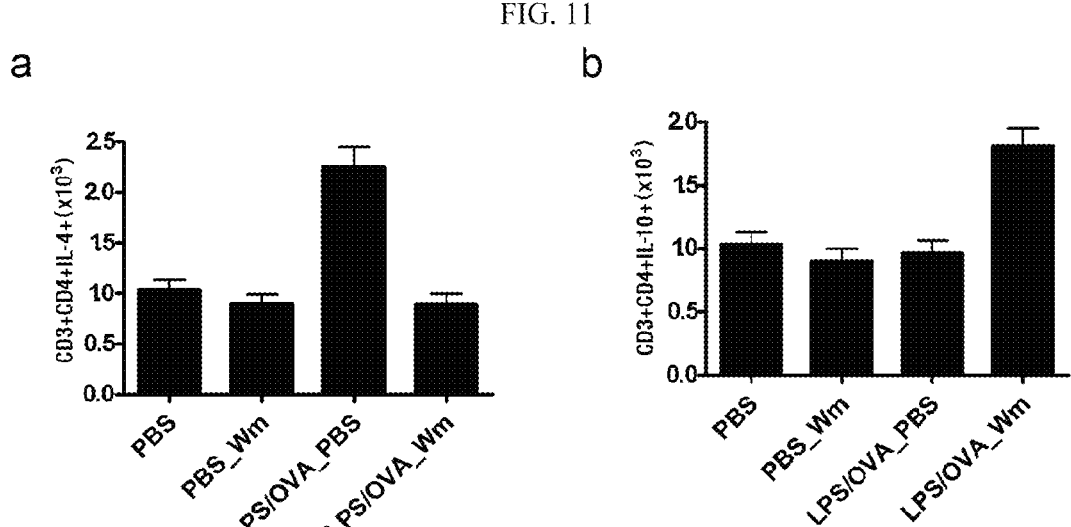
FIGS. 11A and 11b are graphs showing the Th2-mediated immune response assayed in pulmonary tissues of the asthma mouse models intranasally administered with the peptide acting on FPR at 6 hours (Day 22) after the allergen was administered on Day 21.
Figure 12:
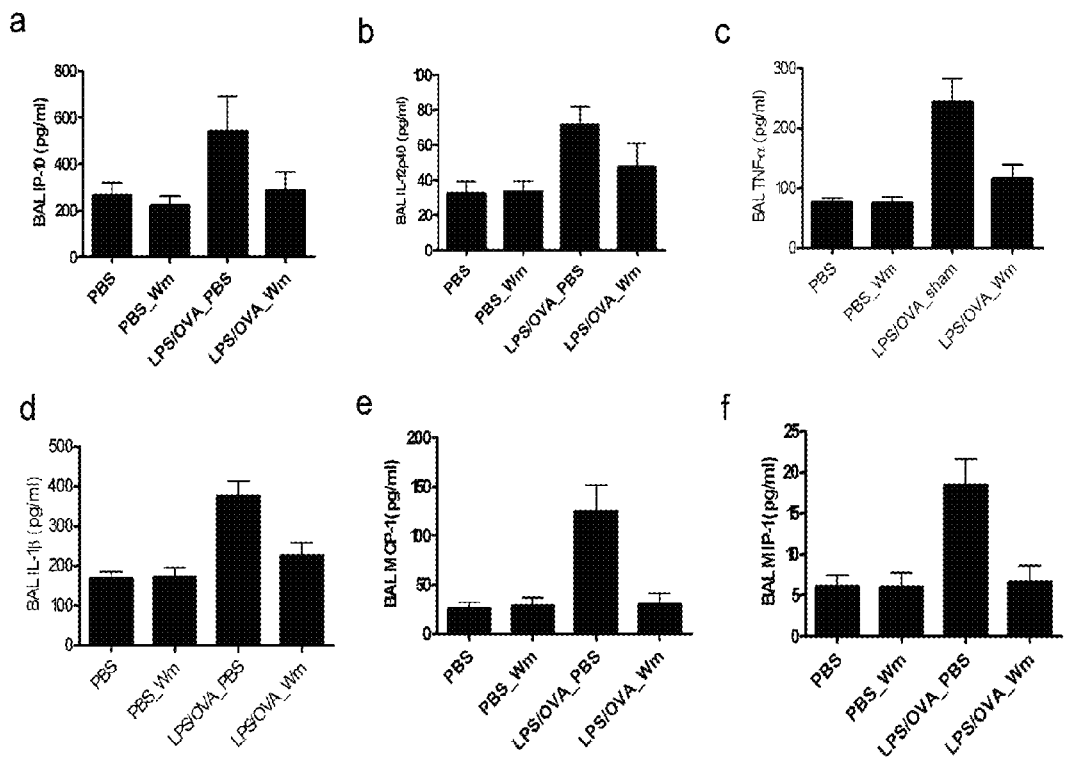
FIGS. 12A-12F are graphs showing the Th1- and Th17-mediated inflammatory cell infiltration and the release of inflammatory mediators from the infiltrated inflammatory cells, assayed in the bronchoalveolar lavage fluid of the asthma mouse models intranasally administered with the peptide acting on FPR at 6 hours (Day 22) after the allergen was administered on Day 21.

FIGS. 8 to 12 show immune response results measured at 6 hours (Day 22) after the final administration of the allergen. There were no differences in the inflammatory cell count of the BAL fluid between the mice intranasally administered with W-peptide (test group) and a sham (positive control) (FIG. 8). Turning to the immunological indices, the release of gamma interferon was increased in the allergen/LPS-sensitized mice, compared to the negative control, as measured in vitro in the Th1 immune response-induced immune cells which were separated from local lymph nodes. Also, the test group intranasally administered with W-peptide was found to release a higher level of gamma interferon than did the positive control intranasally administered with a sham (FIG. 9a). Among inflammatory cells, gamma interferon-expressing CD4+ T cells separated from the pulmonary tissue of the test group intranasally administered with W-peptide were counted and found to be higher than those of the sham-administered positive control (FIG. 9b). However, the level of gamma interferon in the BAL fluid of the test group was rather reduced, compared to that of the positive control (FIG. 9c). In the case of Th17-mediated immune response, when stimulated in vitro with the allergen, immune cells separated from local lymph nodes of the test group were found to have released IL-17 in a higher amount than did those of the positive control (FIG. 10b). Among the inflammatory cells separated from pulmonary tissues, IL-17-expressing CD4+ T cells of the test group were counted and found to be more numerous than those of the positive control (FIG. 10b). However, the level of IL-17 in the BAL fluid of the test group was reduced, compared to that of the positive control (FIG. 10c). As for Th2 cytokines, their expression in T cells of the pulmonary tissues from the test group was reduced, compared to the positive control (FIG. 11a) wherein the expression level of IL-10 was rather increased in the test group (FIG. 11b).

Turning now to the release pattern of inflammation mediators involved in the later inflammatory response, which is responsible for the amplification of inflammation, the release of IP-10 (FIG. 12a) and IL-12p40 (FIG. 12b), which are the downstream molecules of gamma interferon, in the test group was reduced, compared with the positive control. Also, the test group released TNF-α (FIG. 12c) and IL-1β (FIG. 12d), which are regarded as downstream molecules of IL-17, at lower levels than did the positive control. Further, lower levels of MCP-1 (FIG. 12e) and MIP-1a (FIG. 12f), which are Th1- and Th17-induced inflammatory chemokines, were detected in the test group than in the positive control.

Figure 13:
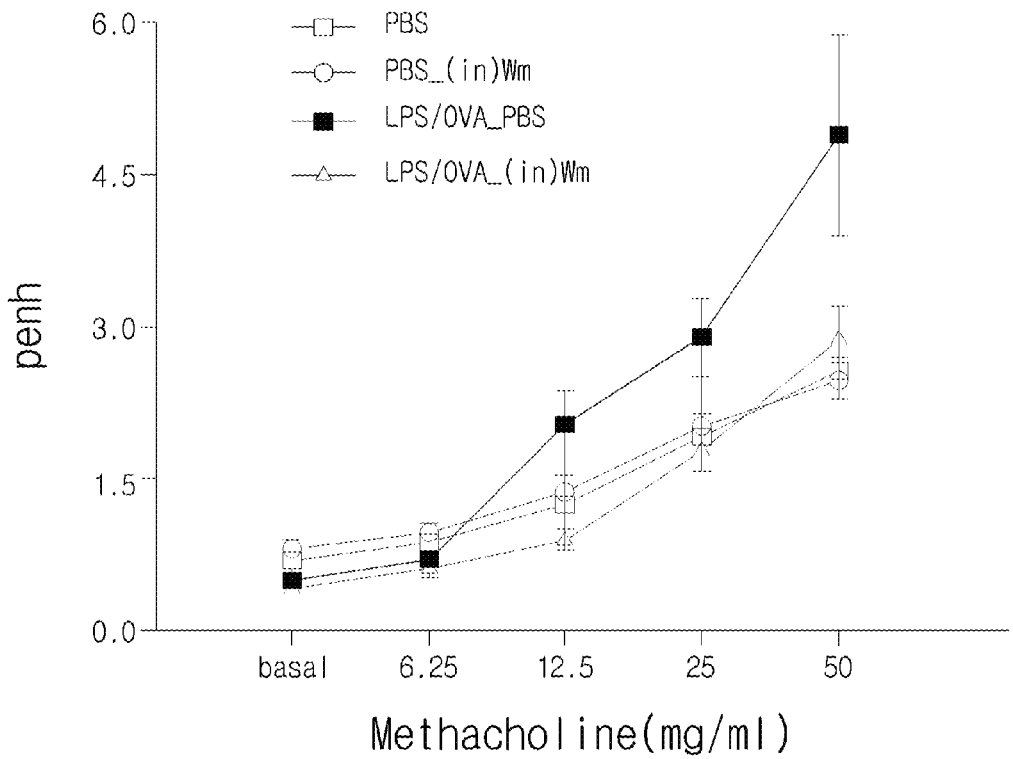
FIG. 13 is of graphs showing the bronchial hypersensitivity of the asthma mouse models intranasally administered with the peptide acting on FPR, measured at 24 hours (Day 23) after the allergen was administered on Day 22.
Figure 14:
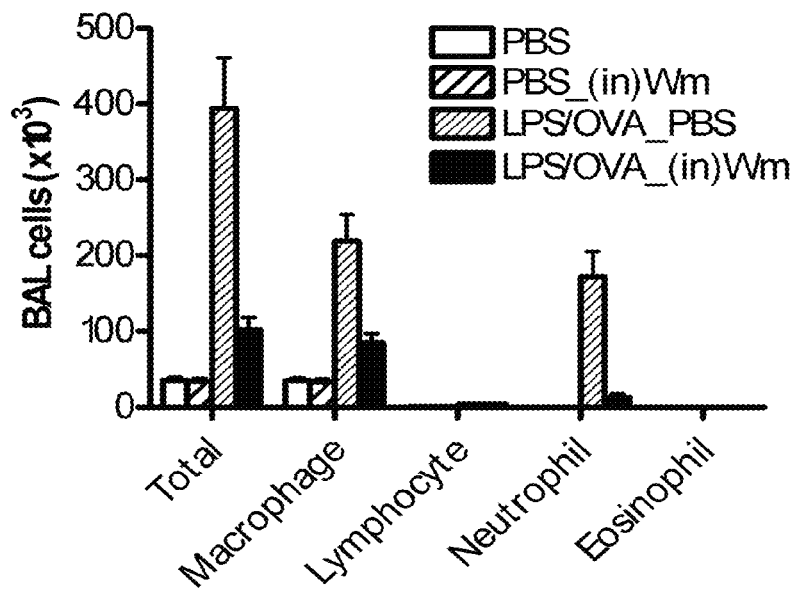
FIG. 14 is of graphs showing the inflammatory response, assayed in the bronchoalveolar lavage fluid of the asthma mouse models intranasally administered with the peptide acting on FPR, at 48 hours (Day 24) after the allergen was administered on Day 22.
Figure 15:
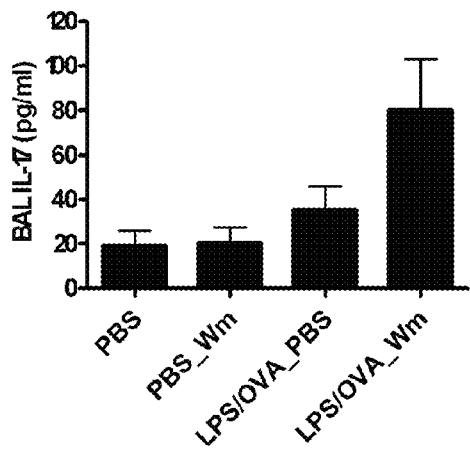
FIGS. 15A-15B are graphs showing the cytokine expression levels from inflammatory cell infiltrated by Th17 immune response, assayed in the bronchoalveolar lavage fluid of the asthma mouse models intranasally administered with the peptide acting on FPR, at 48 hours (Day 24) after the allergen was administered on Day 22.
Figure 15:
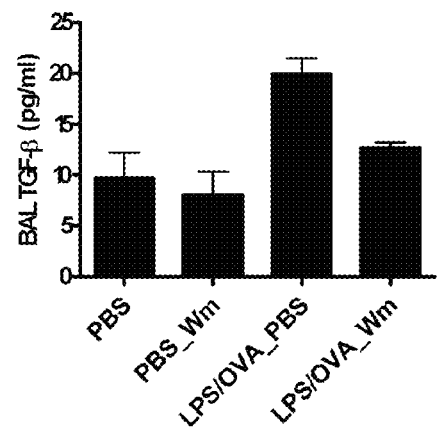
Figure 16:
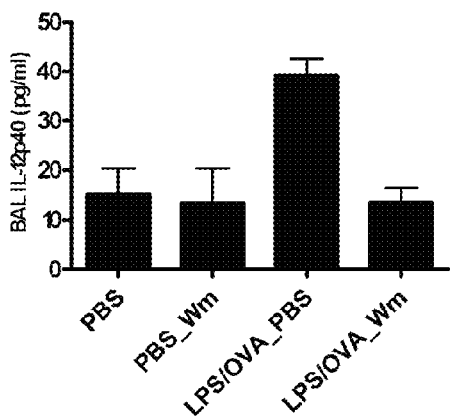
FIGS. 16A-16B are graphs showing the cytokine expression levels from inflammatory cell infiltrated by Th1 immune response, assayed in the bronchoalveolar lavage fluid of the asthma mouse models intranasally administered with the peptide acting on FPR, at 48 hours (Day 24) after the allergen was administered on Day 22.
Figure 16:
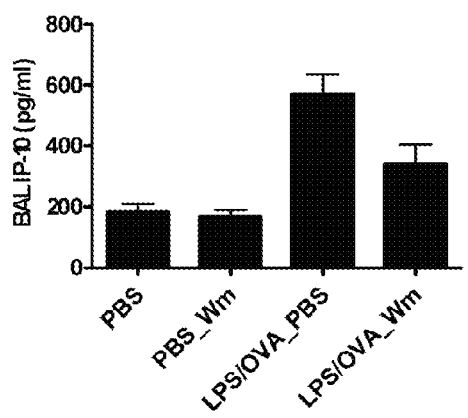

FIG. 13 shows bronchial hypersensitivity measured on Day 23, that is, at 24 hours after the final administration of the allergen. Penh, the index of airway obstruction, was decreased in the test group intranasally administered with WKYMVm, compared to the positive control (FIG. 13). FIGS. 14 to 16 shows immune response results measured on Day 24, that is, at 48 hours after the final administration of allergen. The BAL cellularity, an index of pulmonary inflammation, was significantly reduced in the test group, compared to the positive control (FIG. 14). Also, the release of IL-17, an index of Th-17-mediated immune response, into the BAL fluid was increased in the test group, compared to the positive control (FIG. 15) whereas the release of TGF-β from the inflammatory cells upon IL-17-induced infiltration was significantly reduced in the test group compared to the positive control (FIG. 15b). In addition, higher levels of IL-12p40 (FIG. 16a) and IP-10 (FIG. 16b), which are the cytokines released from the inflammatory cells which infiltrate in response to a Th1-mediated immune response, were detected in the test group than in the positive control.

Taken together, the data obtained from the experiments demonstrate that the direct administration of WKYMVm via the nasal cavity brings about higher suppressive effects on bronchial hypersensitivity and pulmonary inflammation than does the systemic administration thereof. The direct administration can accelerate Th1- and Th17-mediated immune responses while suppressing Th2-mediated immune responses, whereby the infection resulting from the suppression of local Th1- and Th17-mediated immune responses, which is a problem with conventional immune modulators, can be prevented, and with regard to the etiology of asthma and chronic obstructive pulmonary disease, which may be generated by pulmonary inflammation, the direct administration results in higher anti-inflammation effect by effectively suppressing the release of the inflammatory mediators from the inflammatory cells which are induced to infiltrate in response to Th1 and Th17-mediated immune responses.

The above detailed descriptions of embodiments of the invention are not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize.

Accordingly, the actual scope of the invention encompasses the disclosed embodiments and all equivalent ways of practicing or implementing the invention under the claims.

Industrial Applicability

The pharmaceutical preparation, administrable via a respiratory route, comprising as an active ingredient a peptide acting as a ligand to the formyl peptide receptor (FPR) or analogous receptors, exhibits an excellent suppressive effect on respiratory inflammation and thus can be effective for treating or preventing inflammatory respiratory diseases.

The invention claimed is:

1. A method for treating an acute upper respiratory tract infection comprising administering a pharmaceutical preparation comprising a peptide having an amino acid sequence selected from the group consisting of amino acid sequences of SEQ ID NOS: 1 to 3 to a mammalian subject in need thereof via a respiratory route wherein the acute upper respiratory tract infection is selected from the group consisting of a cold, acute pharyngitis, acute rhinitis, acute paranasal sinusitis, acute tonsillitis, acute laryngitis, acute epiglottitis, acute bronchitis and a combination thereof.

2. The method of claim 1, wherein the pharmaceutical preparation is in a form of an aerosol or spray comprising liquid or solid particles.

3. The method of claim 1, wherein the pharmaceutical preparation is in a form of inhalable or respirable particles with a diameter of about 10 μm or smaller.

4. The method of claim 1, wherein the pharmaceutical preparation is in a form of intranasally, intrapulmonarily or intrabronchially administrable particles with a diameter of about 100 μm or smaller.

5. The method of claim 1, wherein the pharmaceutical preparation is administered to the mammalian subject intranasally, intrapulmonarily, by inhalation or by respiration.

6. The method of claim 1, wherein the acute upper respiratory tract infection is a cold.

7. The method of claim 1, wherein the acute upper respiratory tract infection is acute pharyngitis.

8. The method of claim 1, wherein the acute upper respiratory tract infection is acute rhinitis.

9. The method of claim 1, wherein the acute upper respiratory tract infection is acute paranasal sinusitis.

10. The method of claim 1, wherein the acute upper respiratory tract infection is acute tonsillitis.

11. The method of claim 1, wherein the acute upper respiratory tract infection is acute laryngitis.

12. The method of claim 1, wherein the acute upper respiratory tract infection is acute epiglottitis.

13. The method of claim 1 wherein the acute upper respiratory tract infection is acute bronchitis.

14. A method for treating a chronic lower respiratory tract infection comprising administering a pharmaceutical preparation comprising a peptide having an amino acid sequence selected from the group consisting of amino acid sequences of SEQ ID NOS: 1 to 3 to a mammalian subject in need thereof via a respiratory route wherein the chronic lower respiratory tract infection is selected from the group consisting of chronic bronchitis, diffuse panbronchiolitis, bronchiectasis, and a combination thereof.

15. The method of claim 14, wherein the pharmaceutical preparation is in a form of an aerosol or spray comprising liquid or solid particles.

16. The method of claim 14, wherein the pharmaceutical preparation is in a form of inhalable or respirable particles with a diameter of about 10 μm or smaller.

17. The method of claim 14, wherein the pharmaceutical preparation is in a form of intranasally, intrapulmonarily or intrabronchially administrable particles with a diameter of about 100 μm or smaller.

18. The method of claim 14, wherein the pharmaceutical preparation is administered to the mammalian subject intranasally, intrapulmonarily, by inhalation or by respiration.

19. The method of claim 14, wherein the chronic lower respiratory tract infection is chronic bronchitis.

20. The method of claim 14, wherein the chronic lower respiratory tract infection is diffuse panbronchiolitis.

21. The method of claim 14, wherein the chronic lower respiratory tract infection is bronchiectasis.

* * * * *